(12) United States Patent  
Johnson et al.

(10) Patent No.: US 8,062,655 B2
(45) Date of Patent: Nov. 22, 2011

(54) COMPOSITE SCAFFOLD STRUCTURE

(75) Inventors: James R. Johnson, Stillwater, MN (US); Anita Tavakley, Burnsville, MN (US)

(73) Assignee: Phillips Plastics Corporation, Phillips, WI (US)

( * ) Notice: Subject to any disclaimer, the term of this patent is extended or adjusted under 35 U.S.C. 154(b) by 1090 days.

(21) Appl. No.: 11/849,114

(22) Filed: Aug. 31, 2007

(65) Prior Publication Data

US 2009/0062821 A1 Mar. 5, 2009

(51) Int. Cl.
*A61F 2/02* (2006.01)
(52) U.S. Cl. ........................................... 424/426
(58) Field of Classification Search .................. None
See application file for complete search history.

(56) References Cited

U.S. PATENT DOCUMENTS

| | | |
|---|---|---|
| 4,596,574 A | 6/1986 | Urist |
| 5,108,399 A | 4/1992 | Eitenmuller et al. |
| 5,206,023 A | 4/1993 | Hunziker |
| 5,256,418 A | 10/1993 | Kemp et al. |
| 5,270,300 A | 12/1993 | Hunziker |
| 5,410,016 A | 4/1995 | Hubbell et al. |
| 5,597,579 A | 1/1997 | Bezwada et al. |
| 5,607,687 A | 3/1997 | Bezwada et al. |
| 5,641,505 A | 6/1997 | Bowald et al. |
| 5,645,850 A | 7/1997 | Bezwada et al. |
| 5,686,091 A | 11/1997 | Leong et al. |
| 5,770,193 A | 6/1998 | Vacanti et al. |
| 5,770,417 A | 6/1998 | Vacanti et al. |
| 5,837,752 A | 11/1998 | Shastri et al. |
| 5,906,934 A | 5/1999 | Grande et al. |
| 5,939,323 A | 8/1999 | Valentini et al. |
| 6,027,742 A | 2/2000 | Lee et al. |
| 6,103,255 A | 8/2000 | Levene et al. |
| 6,183,737 B1 | 2/2001 | Zaleske et al. |
| 6,210,715 B1 | 4/2001 | Starling et al. |
| 6,281,259 B1 | 8/2001 | Hausdorf et al. |
| 6,333,029 B1 | 12/2001 | Vyakarnam et al. |
| 6,365,149 B2 | 4/2002 | Vyakarnam et al. |
| 6,387,391 B1 | 5/2002 | Shikinami et al. |
| 6,432,435 B1 | 8/2002 | Timmons et al. |
| 6,534,084 B1 | 3/2003 | Vyakarnam et al. |
| 6,575,986 B2 | 6/2003 | Overaker |
| 6,576,015 B2 | 6/2003 | Geistlich et al. |
| 6,623,963 B1 | 9/2003 | Müller et al. |
| 6,635,267 B1 | 10/2003 | Miyoshi et al. |
| 6,656,489 B1 | 12/2003 | Mahmood et al. |
| 6,692,761 B2 | 2/2004 | Mahmood et al. |

(Continued)

FOREIGN PATENT DOCUMENTS

EP 0 360 139 A2 3/1990

(Continued)

OTHER PUBLICATIONS

International Search Report and Written Opinion, obtained from corresponding International Application No. PCT/US2008/074875, Apr. 6, 2009 (9 pgs.).

(Continued)

*Primary Examiner* — Carlos Azpuru
(74) *Attorney, Agent, or Firm* — Holland & Hart LLP

(57) ABSTRACT

A composite resilient scaffold may be used to grow, repair, and/or regenerate tissue such as articular cartilage. The composite scaffold is porous and at least substantially bioremovable. The composite scaffold includes a support structure coated with a discontinuous coating of separate and discrete particles of a ceramic material such as calcium phosphate. The calcium phosphate material may have a porous reticulated structure.

25 Claims, 2 Drawing Sheets

U.S. PATENT DOCUMENTS

| | | |
|---|---|---|
| 6,736,799 B1 | 5/2004 | Erbe et al. |
| 6,773,713 B2 | 8/2004 | Bonassar et al. |
| 6,815,179 B2 | 11/2004 | Ochi et al. |
| 6,852,331 B2 | 2/2005 | Lai et al. |
| 6,972,130 B1 | 12/2005 | Lee et al. |
| 7,112,417 B2 | 9/2006 | Vyakarnam et al. |
| 7,198,908 B2 | 4/2007 | Ochi et al. |
| 7,201,917 B2 | 4/2007 | Malaviya et al. |
| RE39,713 E | 7/2007 | Sawhney et al. |

FOREIGN PATENT DOCUMENTS

| | | |
|---|---|---|
| EP | 0 469 070 B1 | 2/1992 |
| EP | 0 677 297 A1 | 10/1995 |
| EP | 0 714 666 A1 | 6/1996 |
| EP | 1 027 897 A1 | 8/2000 |

OTHER PUBLICATIONS

Kalita, S.J., Ferguson, M., Am .J. Biochem. & Biotechnol., 2006, 2, pp. 57-60 (4 pages).

SHAPED FORM CUT FROM MOLDED PIECE

PIECES FROM WHICH A SURGEON COULD CUT A SHAPE (OR HAVE IT DONE)

OPEN PORE TYPES, ETC.   DISCS   TABS

CELLS/CARTILAGE

TCP COATED ON A STRUT

TCP
PLA-PGA "GLUE"
STRUT

THE IMPLANT

COMPOSITE SCAFFOLD STRUCTURE

BACKGROUND

Articular cartilage covers the ends of all bones that form articulating joints in humans and animals. The articular cartilage acts in the joint as a mechanism for force distribution and as a bearing surface between different bones. Without articular cartilage, stress concentration and friction would occur to the degree that the joint would not move easily. Loss of the articular cartilage usually leads to painful arthritis and decreased joint motion.

Articular cartilage is characterized by a structural organization that includes specialized cells (chondrocytes) embedded in an intercellular material which is rich in proteoglycans, collagen fibrils of predominantly type II, other proteins, and water. Cartilage tissue is neither innervated nor penetrated by the vascular or lymphatic systems. However, in the mature joints of adults, the underlying subchondral bone tissue, which forms a narrow, continuous plate between the bone tissue and the cartilage, is innervated and vascularized. Beneath this bone plate, the bone tissue forms trabeculae, containing the marrow. In immature joints, articular cartilage is underlined by only primary bone trabeculae. A portion of the meniscal tissue in joints also consists of cartilage whose make-up is similar to articular cartilage.

Articular cartilage may be damaged by a traumatic injury or from degenerative conditions such as arthritis or osteoarthritis. The inability of articular cartilage to self-repair is a major problem in treating patients having an articular cartilage defect. Over the years a number of treatments have been developed in attempts to repair and/or regenerate articular cartilage. For example, one type of treatment includes subchondral drilling and abrasion. Unfortunately, treatments of this nature are ineffective in the long term because they do not promote formation of new or replacement cartilage tissue or cartilage-like tissue. Instead, these treatments result in the formation of scar or fibrous tissue, which cannot withstand long term joint loading. Thus, although the condition of patients treated using these technique initially improves, eventually it will deteriorate, possibly leading to osteoarthritis.

Another conventional therapy relied on for treating loss of cartilage is replacement with a prosthetic material, such as silicone for cosmetic repairs, or metal alloys for joint realignment. Placement of prostheses is commonly associated with significant loss of underlying tissue and bone without recovery of the full function allowed by the original cartilage, as well as the irritating presence of a foreign body. Other long term problems associated with a permanent foreign body can include infection, erosion, and instability.

More recently, new approaches to cartilage tissue repair have been proposed. One approach is based on implanting or injecting cells into a defect in a patient's cartilage tissue. The implant may include biocompatible synthetic polymeric support structures seeded with chondrocytes, fibroblasts, or bone-precursor cells. Although these approaches have served to further improve treatment of damaged cartilage, there are still a number of problems associated with them. For example, it is difficult to successfully grow the desired quantity and quality of cells on such support structures. Also, the implants may not have sufficient mechanical properties to withstand the loading and other stresses place thereon in the joint.

Accordingly, it would be desirable to provide an improved scaffold that is biocompatible and better facilitates repair and/or regrowth of articular cartilage.

SUMMARY

A variety of embodiments of composite open pore resilient scaffolds are described herein that may be used to grow, repair, and/or regenerate tissue such as cartilage, bone tissue, and the like. The composite scaffolds may serve as a temporary structure that facilitates cellular growth either in vivo or in vitro. The composite scaffold is preferably used to grow chondrocytes but can also be used to grow any other cells such as fibroblasts, bone-precursor cells, and the like. It should be appreciated that the term "resilient" is used herein to refer to a product or material that springs back, rebounds, or returns substantially to its original form after being compressed, bent or stretched.

In one embodiment, the composite open pore resilient scaffold may be implanted in a joint to facilitate repair and/or regeneration of damaged articular cartilage. The composite scaffold may have sufficient mechanical strength for it to be utilized for cell growth in joints while at the same time withstanding joint loading. The composite scaffold may be especially useful for cartilage replacement therapies where there is little or no existing cartilage tissue because the cell-saturated composite scaffold forms a cushioning and shock-absorbing layer while the cells are held in place.

The composite open pore resilient scaffold includes a support structure and a dispersed particle coating of ceramic material over the support structure. The support structure and/or the particles of ceramic material are porous to provide a high surface area three-dimensional structure that promotes cell growth. Preferably, the exterior surfaces and the interior surfaces (i.e., inside the pores) may be coated with the ceramic material. The ceramic material may be included to provide a beneficial environment that promotes cell growth. In a preferred embodiment, the ceramic material includes calcium phosphate material.

The coating of ceramic material is provided as a light coating of separate and discrete particles or separate and discrete clumps of particles that form a discontinuous coating over the surface of the support structure. This type of coating allows the composite scaffold to flex and bend without causing the ceramic material to break and fall off. In contrast, a continuous coating of ceramic material has very little flexibility which means that it is much more prone to breaking and spalling off when the composite scaffold flexes and bends. The particles of ceramic material may be powder or flakes.

The composite scaffold may be easy to shape to accommodate any patient or implant site. The composite scaffold may be shaped before the cells are grown on the material. The shape of end product of the composite scaffold can also be determined by the shape of the cell culture well. FIG. 1 shows a number of embodiments of suitable shapes for the composite scaffold.

In one embodiment, the composite scaffold is biocompatible which means that it has no or negligible in vivo toxicity and is compatible with in vivo conditions. The preferred composite scaffold is also bioremovable because it degrades and is incorporated into or removed from the body. It should be appreciated that the term "bioremovable" is used herein to refer to biocompatible materials that are capable of being gradually absorbed by the body, gradually removed by the body, broken down and absorbed by the body, broken down and removed by the body, and/or otherwise used by or eliminated from the body. Thus, bioremovable materials may be removed by processes such as bioabsorption (i.e., the materials are absorbed by the body and moved within the body to be used by the body) and/or biodegradation (i.e., the materials chemically fall apart into components that are carried away by the body) as well as other like processes. (i.e., has no or negligible in vivo toxicity and is compatible with in vivo conditions)

In one embodiment, the composite scaffold may be seeded with cells prior to being implanted in the patient. This allows the composite structure to be pre-loaded with cells that are successfully growing before the composite structure is implanted.

The composite scaffold may also include bioactive agents that are released over time. For example, in one embodiment, the bioactive agents may be released immediately and for a short duration after the composite scaffold has been put in position (e.g., 1-10 days release time). In another embodiment, the bioactive agents may be released slowly as the composite scaffold degrades in vivo. These release means may be accomplished by incorporating the bioactive agents in the support structure of the composite scaffold so that the bioactive agents are slowly released as the support structure degrades or on the surface of the support structure, or in the pores of the attached ceramic particles for other desired release rates.

Suitable bioactive agents that may be included with the composite scaffold include antiinfectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-.beta. I-III), vascular endothelial growth factor (VEGF)); and other naturally derived or genetically engineered proteins, polysaccharides, glycoproteins, or lipoproteins.

The composite scaffold may be used as a therapeutic, structural, or cosmetic implant. The composite scaffold may also be used to grow cells in vivo and/or in vitro. A method of making the composite open pore resilient scaffold includes making a reticulated form by assembling a form from rods, fibers, and the like, or by injection molding the support structure and coating the interior and exterior surfaces of the support structure with the ceramic material using a fluidized bed.

The foregoing and other features, utilities, and advantages of the subject matter described herein will be apparent from the following more particular description of certain embodiments as illustrated in the accompanying drawings.

DRAWINGS

DETAILED DESCRIPTION

Figure 1:
FIG. 1 shows various embodiments of composite scaffolds having various shapes.
Figure 1:
Figure 1:
Figure 1:
Figure 1:
Figure 1:
Figure 1:
Figure 1:
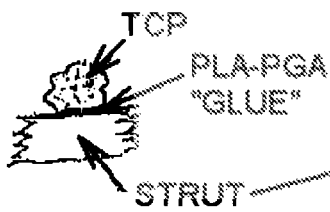
Figure 1:

A composite scaffold is shown and described herein that can be used to repair and/or regenerate tissue. The composite scaffold may be used in a number of ways to repair and/or regenerate tissue including, but not limited to, (i) growing cells in vitro on the composite scaffold and then implanting the composite scaffold into a patient, or (ii) implanting the composite scaffold into a patient and then infusing cells in situ around the composite scaffold. Preferably, the composite scaffold is used as an implant (either with or without an initial seeding of cells) to grow cartilage in situ that provides a permanent cartilage replacement. For example, the composite scaffold may be implanted in a joint to facilitate the repair and/or regeneration of articular cartilage tissue that has deteriorated, been torn, is absent, or otherwise damaged.

It should be appreciated that although the following discussion is primarily focused on repairing and regenerating articular cartilage, the composite scaffold may also be used to repair and/or regenerate a wide variety of other tissue. The principles explained in connection with repairing and/or regenerating articular cartilage apply directly or by analogy to growing and repairing other tissue. Other tissue that may be grown, repaired, or regenerated using the composite scaffold include bone, spine disc, meniscus, fibrocartilage, tendons, ligaments, and soft tissue organs. In the latter, the modulus of the resilient form may be much lower (softer) and the dispersed particles may be other materials than calcium phosphate.

The composite scaffold is flexible, bioremovable, and biocompatible. The composite scaffold includes a support structure or support scaffold that is coated with a ceramic material such as calcium phosphate material. The composite scaffold is porous and has a high amount of surface area for the calcium phosphate material to adhere to and for cells to grow on. The composite scaffold is preferably a fully open-pore material with pore sizes suitable to allow cells to grow in and around the entire network of struts. The composite scaffold may also be flexible and resilient enough to provide cushioning in areas where cartilage repair and/or regeneration is needed.

The support structure may be a substantially homogenous structure provided with small holes or pores that are sized to allow nutrients and waste products to move to and from cells coupled to the composite scaffold. The open pore network may also be sized to permit vascularization. In one embodiment, the support structure may have a reticulated porous structure where the pores form a network of interconnected openings extending throughout the support structure and opening to the exterior surface. Thus, a reticulated porous structure is a structure made up of a network of interconnected struts that form a strong, interconnected continuum of pores.

The porosity characteristics of the support structure (e.g., macroporosity percentage, pore size, and the like) may be chosen to provide the necessary mechanical strength and to allow nutrients and other materials to diffuse into and out of the pores thereby facilitating cell growth. In one embodiment, the support structure may have a macroporosity of approximately 25% to 85%, approximately 50% to 85%, or, desirably, approximately 55% to 85%. Also, the mean size of the pores in the support structure may be approximately 50 microns to 500 microns, approximately 30 microns to 500 microns, or, desirably, approximately 100 microns to 500 microns. The mean size of the pores in the support structure may also be at least approximately 10 microns, at least approximately 100 microns, at least approximately 150 microns, or, desirably, at least approximately 250 microns. The larger pore sizes accommodate vascularization.

The support structure may be formed from any one or combination of suitable polymeric materials. Preferably, the support structure is at least substantially bioremovable. Thus, the support structure may include one or more bioremovable polymeric materials. The selection of a suitable polymeric material depends on several factors. The chemical composition, spatial distribution of the constituents, molecular weight, and degree of crystallinity all influence to some extent the in-vitro and in-vivo behavior of the polymeric material. However, the selection of the polymeric material used to make the support structure for tissue repair and/or regeneration largely depends on, but is not limited to, the following factors: (i) bioremoval kinetics, (ii) in-vivo mechanical performance, (iii) cell response to the material in terms of cell attachment, proliferation, and migration, and (iv) biocompatibility.

It is generally desirable to select the bioremovable polymeric material to facilitate the timely degradation and removal of the support structure in the body environment. Different polymeric materials having different absorption times under in-vivo conditions can be combined to provide the support structure with the desired degradation characteristics. For example a copolymer of 35:65 ε-caprolactone and glycolide (a relatively fast absorbing polymer) may be blended with 40:60 ε-caprolactone and (L)lactide copolymer (a relatively slow absorbing polymer) to form the support structure. Such a support structure can have several different physical structures depending upon the processing technique used. The two polymeric components can be either randomly inter-connected bicontinuous phases, or the components can have a gradient through the thickness or a laminate type composite with a well integrated interface between the two components. The microstructure of these support structures can be optimized to regenerate and/or repair the desired anatomical features of the tissue. In one embodiment, the support structure may degrade within approximately four to twenty-four weeks.

It should be appreciated that the support structure be made of any suitable bioremovable material. The support structure may include synthetic polymeric material, natural polymeric material (e.g., biopolymers), and/or a combination of both. Synthetic polymeric material may be desirable because the rate at which it degrades can be more accurately determined and it has more lot to lot consistency and less immunogenicity than natural polymers. Examples of suitable synthetic polymeric materials include polymers of hydroxy acids such as polylactic acid (PLA), polyglycolic acid (PGA), and polylactic acid-glycolic acid (PLGA), polycaprolactone, polyorthoesters, polyanhydrides, polyphosphazenes, and combinations thereof. Examples of suitable natural polymeric materials include proteins such as collagen, albumin, and fibrin; and polysaccharides such as alginate and polymers of hyaluronic acid.

Elastomeric copolymers may also be particularly useful in the support structure to provide the desired amount of flexibility and resiliency. Suitable bioremovable, biocompatible elastomers include but are not limited to elastomeric copolymers of ε-caprolactone and glycolide (desirably having a mole ratio of ε-caprolactone to glycolide of from about 35:65 to about 65:35, more desirably from 45:55 to 35:65), elastomeric copolymers of ε-caprolactone and lactide, including L-lactide, D-lactide blends thereof or lactic acid copolymers (desirably having a mole ratio of ε-caprolactone to lactide of from about 95:5 to about 85:15, desirably from about 35:65 to about 65:35, and more desirably from 45:55 to 30:70).

The elastomeric polymers may exhibit a high percent elongation and a low modulus, while possessing good tensile strength and good recovery characteristics. In some embodiments, the elastomeric polymers from which the support structure is formed may exhibit a percent elongation greater than about 200% and desirably greater than about 500%. These properties, which measure the degree of elasticity of the bioremovable elastomer, may be achieved while maintaining a tensile strength greater than about 500 psi, desirably greater than about 1,000 psi, and a tear strength of greater than about 50 lbs/inch, desirably greater than about 80 lbs/inch. It should be appreciated that the resilient properties (e.g., amount of resiliency) of the support structure can be modified by tailoring the polymeric materials accordingly. The polymeric materials may be selected to achieve various moduli of elasticity for different applications.

The polymeric material used to form the support structure may be rendered porous using any suitable process such as lyophilization, supercritical solvent foaming, gas injection extrusion, gas injection molding, injection molding, or casting with an extractable material (i.e., salts, sugar or any other suitable materials). In one embodiment, bioremovable, biocompatible polymeric support structures may be made porous using the injection molding techniques described in U.S. patent application Ser. No. 11/848,163, entitled "Methods, Tools, and Products for Molded Ordered Porous Structures,", filed on 30 Aug. 2007, and naming Majid Entezarian et al. as inventors, which is incorporated herein by reference in its entirety.

It should be appreciated that numerous other methods may be used to make the porous support structure. For example, in another embodiment, the porous support structure may be made by a polymer-solvent phase separation technique. Generally, a polymer solution can be separated into two phases by any one of the following four techniques: (a) thermally induced gelation/crystallization; (b) non-solvent induced separation of solvent and polymer phases; (c) chemically induced phase separation, or (d) thermally induced spinodal decomposition. The polymer solution is separated in a controlled manner into either two distinct phases or two bicontinuous phases. Subsequent removal of the solvent phase may leave a porous structure of density less than the bulk polymer and pores in the micrometer range. The steps involved in the preparation of these support structures include choosing the appropriate solvent for the polymers that need to be lyophilized and preparing a homogeneous solution of the polymers and the solvent. Next, the solution is subjected to a freezing and vacuum drying cycle. The freezing step separates the polymer solution and the vacuum drying step removes the solvent by sublimation and/or drying. The result is a porous polymeric support structure that has a plurality of interconnected open cells.

In some embodiments, one or more additives may be added to the support structure. Typically, such additives are included as a solid that is mixed with the polymer feedstock fed to the injection molding process or with the polymer-solvent system, depending on which technique is used. Typically the additives are solid although it is contemplated that liquid additives may also be used. The additives may be selected so that they do not react with the polymer or the solvent. The additives may serve any of a number of advantageous functions. For example, the additives may serve to provide mechanical strength to the support structure, alter the resilient properties of the support structure to reach a desired resiliency, change the rate at which the support structure degrades in vivo, act as a bioactive agent, or otherwise modify or change the properties of the support structure or the resulting composite scaffold in an advantageous manner. Examples of suitable additives that may be used include materials that promote tissue regeneration or regrowth, buffers, reinforcing materials, diluents, carriers, excipients, stabilizers, porosity modifiers, and the like. In one embodiment, the support structure may include bone repair additives such as calcium phosphate particles, or calcium carbonate particles, pore creation additives such as leachable solid materials, or reinforcing additives such as particles of insoluble bioremovable substances.

Suitable leachable solid materials include nontoxic leachable materials such as salts (e.g., sodium chloride and the like), sugars, and gelatins. The leachable solid materials may be included as particles that have an average diameter of less than approximately 1 mm and desirably have an average diameter of approximately 50 microns to about 500 microns. The particles may constitute approximately 1 to 90 volume percent of the total volume of the particle and polymer-solvent mixture (wherein the total volume percent equals 100 volume percent). The leachable materials can be removed by exposing the leachable material to a solvent under appropriate conditions and for a sufficient amount of time to dissolve the leachable material. The solvent is selected so that it does not affect the polymeric material that is intended to form the finished support structure. In one embodiment, the extraction solvent may be water, desirably distilled-deionized water. If water is used as the solvent, the support structure may be dried after the leaching process is complete at low temperature and/or vacuum to minimize hydrolysis of the structural polymeric material unless accelerated degradation of the support structure is desired.

As already mentioned, the exposed surfaces (interior and exterior surfaces) of the support structure may be coated with calcium phosphate material to facilitate cell growth on the composite scaffold. The presence of calcium phosphate material on the support structure is beneficial to the attachment and growth of cells on the composite scaffold. The larger porosity of the support structure and the smaller porosity of the calcium phosphate particles are both accessible to and facilitate the growth of the cells. The coating of calcium phosphate powder not only provides a favorable environment for cell growth, its surface may be treated to hold fluids or other solid or liquid materials that promote cell growth or differentiation in stem cells. The calcium phosphate is not only compatible with the cells but is also compatible with a wide array of biologically active agents that may be included with the composite scaffold. The calcium phosphate material can be employed as part of the composite scaffold to deliver bioactive agents or cells to any of a variety of sites in the body, or can be used in vitro. Any suitable bioremovable calcium phosphate material may be used. Examples of suitable calcium phosphate material include tricalcium phosphate and amorphous hydroxyapatite. In a preferred embodiment, the calcium phosphate material has a calcium to phosphate ratio of approximately 1.3 to 1.5.

The attached particles of calcium phosphate may be distributed over the surface of the support structure's struts (interior and exterior) such that the resilient nature of the support structure is preserved. This may be accomplished by applying the calcium phosphate as a discontinuous coating over the support structure. By referring to the coating as a discontinuous coating, it is meant that the calcium phosphate is provided as a coating of separate and discrete particles of calcium phosphate and/or separate and discrete clumps of particles of calcium phosphate. The particles and/or clumps of particles are spaced apart a sufficient distance to allow the support structure to flex and bend without causing substantial amounts of the calcium phosphate material to break and/or fall off the support structure. In contrast, a continuous coating of calcium phosphate material may form a brittle outer shell that can crack, break, and flake off as the composite scaffold flexes and bends under ordinary stresses inside a joint.

The particles of calcium phosphate material may be porous. The porous nature of the particles of calcium phosphate material may increase the surface area of each particle and consequently the bioavailability of the calcium phosphate material to the cells growing on the composite scaffold. Also, the pores in the calcium phosphate particles may be capable of holding various bioactive agents as well as other desirable materials. Each particle of calcium phosphate material is preferably a fully open-pore material with pore sizes suitable to allow incorporation of the bioactive agents. In one embodiment, the particles of calcium phosphate material may have a reticulated porous structure where the pores form a network of interconnected openings extending throughout the particle and opening to the exterior surface of the particle. Thus, the reticulated structure is a structure made up of a network of interconnected struts that form a strong, interconnected continuum of pores. The mean size of the pores in the particles of calcium phosphate material may be approximately 0.01 microns to 10 microns, approximately 0.01 microns to 5 microns, or, preferably, 0.01 microns to 1 micron.

The calcium phosphate material is bioremovable. Although a number of calcium phosphate compounds have been referred to in the literature as "resorbable," such compounds, usually comprising or derived from tricalcium phosphate, tetracalcium phosphate or hydroxyapatite, are in fact only weakly resorbable. Of the group, the tricalcium phosphate compounds have been demonstrated to be the most resorbable. Tricalcium phosphate is cited to often have lengthy and somewhat unpredictable resorption profiles, sometimes requiring in excess of one year to resorb. The small particle size of the calcium phosphate material increases the rate of bioabsorbtion as does also using very high surface area nanopore materials.

One way to overcome the relatively slow degradation times of some calcium phosphate materials is to apply the calcium phosphate material as a discontinuous coating. As the support structure degrades, the particles of calcium phosphate material are released from the underlying support structure as relatively small individual particles or relatively small clumps of particles that continue to bioabsorb over time. Also, the calcium phosphate material may still be available as individual particles at the implant site to continue to promote cell growth. In contrast, a continuous coating of calcium phosphate material is more problematic because it is more likely to form an outer shell that is resistant to degradation long after the underlying support structure has degraded. Also, when it does degrade, a continuous coating is more likely to break into large chunks that may cause problems at the implant site.

Figure 2:
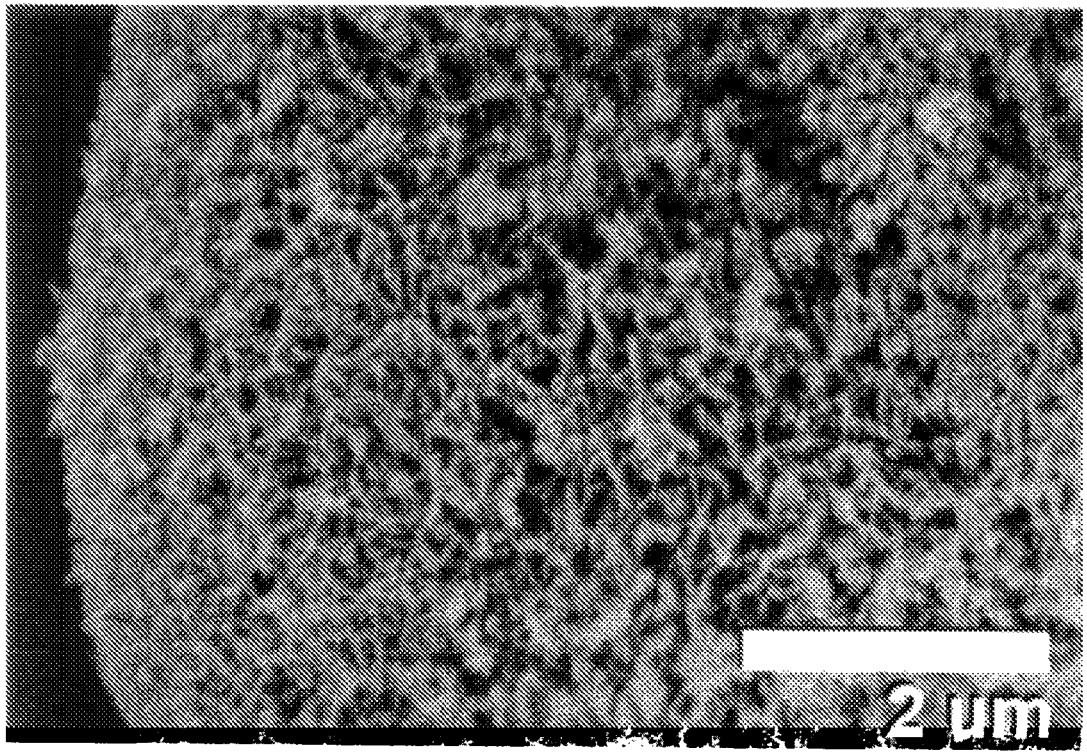
FIG. 2 is a micrograph of a particle of amorphous calcium phosphate which shows that the particles are porous and have a high amount of surface area.

The size of the calcium phosphate particles and the type of calcium phosphate material may be selected to provide the desired degradation time. The size of the calcium phosphate particles may be approximately 0.1 to 5.0 microns and preferably 0.1 to 1 micron. In one embodiment the calcium phosphate material may include amorphous calcium phosphate (ACP) that has a very high surface area compared to the support structure. The amorphous calcium phosphate also has poor crystallinity. FIG. 2 shows the pore structure of one embodiment of amorphous calcium phosphate with a surface area of about 800 square meters per gram.

The use of the term "amorphous" is meant to refer to a material with significant amorphous character. Significant amorphous character contemplates greater than 75% amorphous content, preferably greater than 90% amorphous content, and is characterized by a broad, featureless X-ray diffraction pattern that reveals its poor crystallinity. It is recognized that a small degree of crystallinity may exist in the material.

The composite scaffold as a whole may have a number of desirable properties. For example, the composite scaffold may be designed to have stiffness and compressibility properties that are similar to the respective cartilage and bone tissue in the relevant joints being repaired. The composite scaffold may also be at least substantially bioremovable. As already described, the support structure and the calcium phosphate material may be bioremovable which renders the majority of the composite scaffold bioremovable. Also, other materials included in the composite scaffold may degrade and be removed by or absorbed into the body. For most applications, especially in vivo applications, it is desirable for all or substantially all of the composite scaffold to be bioremovable. However, there may be instances where it is desirable to include small amounts of certain materials or bioagents that are not bioremovable but provide some other beneficial characteristic or feature to the composite scaffold. Even in these situations, it may be desirable to minimize the amount of non-bioremovable material.

In one embodiment, the rate that the composite scaffold breaks down may be similar or identical to the rate at which the body generates autogenous tissue providing sufficient mechanical strength to replace the composite scaffold. As already mentioned above, the rate at which the composite scaffold breaks down can be altered by changing the composition of the materials used in the composite scaffold, and in particular, the composition of the polymeric materials used as the support structure. The ratio and types of bioremovable polymeric material included in the support structure may be altered to speed up or slow down the rate at which the composite scaffold breaks down. The method of manufacture of the bioremovable polymeric material can also be used to alter the rate of degradation.

The composite scaffold may break down over a time period of less than a year, desirably, less than six months, and, more desirably, in approximately four to ten weeks. In the case of joint surface application, the degradation period may be approximately twelve to twenty-four weeks. In the case where weight bearing or high shear stress is not an issue, the degradation period may be approximately five to ten weeks.

In one embodiment, the composite scaffold may be seeded with cells prior to being implanted into a patient. The cells may be any type of cells commonly occurring in articular cartilage or any type of cells capable of differentiating into cells commonly occurring in articular cartilage. In one embodiment, the cells are chondrocytes that are suitable to use to repair and/or regenerate articular cartilage. Other suitable cells that may be seeded on to the composite scaffold include, but are not limited to, osteocytes, osteoblast (i.e. bone cells), mesenchymal stem cells, other bone- or cartilage-producing cells or cell lines, fibroblasts, and muscle cells. The cells may also contain inserted DNA encoding a protein that stimulates the attachment, proliferation or differentiation of tissue.

It should be appreciated that various cells can be used with the composite scaffold (e.g., autologous cells, allogeneic cells, xenogeneic cells, or syngeneic cells, etc.). It is preferred to use autologous cells, thus minimizing, or even excluding, the chance of rejection responses in or disease transmission to the patient treated with the composite scaffold. In one embodiment, cells can be harvested from the patient (before or during surgery to repair the tissue) and the cells can be processed under sterile conditions to provide a specific cell type. Where the cells are not autologous, it may be desirable to administer immunosuppressive agents in order to minimize rejection. In preferred embodiments, such agents may be included within the seeded composition to ensure effective local concentrations of the agents and to minimize systemic effects of their administration. The cells employed may be primary cells, explants, or cell lines, and may be dividing or non-dividing cells. Cells may be expanded ex vivo prior to introduction into the composite scaffold. Autologous cells are preferably expanded in this way if a sufficient number of viable cells cannot be harvested from the host.

Seeding the composite scaffold with cells may be carried out in any suitable manner. The composite scaffold may be seeded with cells using static or dynamic seeding techniques. For example, the composite scaffold may be placed in a cell culture and the cells seeded onto and/or into the composite scaffold. After the cells are initially seeded, the cells are preferably cultured in vitro to allow for a sufficient degree of proliferation of the cells. The culturing period may vary broadly and range between one hour and several months depending on the number of seeded cells and the size of the composite scaffold implant. In one embodiment, the composite scaffold is maintained in a sterile environment and then implanted into the patient once the cells have invaded the pores of the composite scaffold. In vitro seeding of cells may provide for a more rapid development and differentiation process for the tissue. It is clear that cellular differentiation and the creation of tissue specific extracellular matrix is of considerable importance to engineer a functional tissue implant.

In one embodiment, a biphasic or high order tissue structure may be created using the composite scaffold. This may be done by initially seeding different cell types into separate composite scaffolds. The composite scaffolds can be combined after a short period of time and the entire structure can be placed back in cell culture to form a biphasic tissue structure that can be implanted into the patient. Also, radio-opaque markers may be added to the composite scaffolds to allow them to be easily imaged after implantation. If an acellular strategy is pursued, then the sterile acellular scaffolds would be used to replace damaged or traumatized tissue.

Any preparation of living cells may be use to seed the composite scaffold. For example, cultured cells or isolated individual cells may be used. Alternatively or additionally, pieces of tissue, including tissue that has some internal structure, may be used. The cells may be primary tissue explants and preparations thereof, cell lines (including transformed cells), or host cells. Where the cells are host cells and are introduced into the composite scaffold in vivo, preferred sources of cells include, but are not limited to, the inner layer of the periosteum or perichondrium, blood or other fluids containing the cells of choice, and damaged host tissue (particularly bone or cartilage) that includes such cells. Any available methods may be employed to harvest, maintain, expand, and prepare cells for use with the composite scaffold.

Of course, the composite scaffold is not limited to using tissue-producing cells. Certain preferred embodiments utilize such cells primarily because the composite scaffold is so well suited to tissue-regeneration applications (particularly with those involving growth of bone and/or cartilage). However, it should be appreciated that any cell may be seeded into the composite scaffold. In some cases, it may be desirable to include other cells in addition to tissue-producing cells.

The composite scaffold may also include any one or combination of a number of bioactive agents (also referred to as therapeutic agents). The term "bioactive agent" includes pharmacologically active substances that produce a local or systemic effect in a patient. The term thus means any substance intended for use in the diagnosis, cure, mitigation, treatment or prevention of disease or in the enhancement of desirable physical or mental development and conditions in a patient.

It should be appreciated that virtually any bioactive compound useful in the composite scaffold or in the environment of the composite scaffold may be coated onto the composite scaffold. In one embodiment, bioactive molecules that have specific effects on ingrowing cells may be coated onto the composite scaffold. Such molecules can be those that effect cell migration, cell adhesion, cell commitment, cell proliferation, cell differentiation, etc. Such molecules include interlukins, interferons, bone morphogenetic factors, growth factors including platelet-derived growth factor, epidermal growth factor, transforming growth factor and fibroblast growth factor and colony stimulating factors. In one embodiment, bioactive agents which may be administered via the composite scaffold include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-.beta. I-III), vascular endothelial growth factor (VEGF)); and other naturally derived or genetically engineered proteins, polysaccharides, glycoproteins, or lipoproteins. A list of additional bioactive agents that may be included in the composite scaffold includes those listed in U.S. Pat. No. 6,972,130, which is hereby incorporated herein by reference.

The composite scaffold may be used as a medical implant to repair and/or regenerate tissue such as cartilage. The medical implant may be used in situations where the cartilage of a patient has been damaged as a result of inflammation, trauma, aging, or congenital defects.

The composite scaffold may be sterilized using conventional sterilization process such as radiation based sterilization (i.e. gamma-ray), chemical based sterilization (ethylene oxide) or other appropriate procedures. In one embodiment, the sterilization process may use ethylene oxide at a temperature between 52-55° C. for a time of 8 hours or less. After sterilization the composite scaffold may be packaged in an appropriate sterile moisture resistant package for shipment and use in hospitals and other health care facilities.

The composite scaffold may be made using any suitable method or technique. The process of making the composite scaffold typically involves making the support structure first and then coating it with the calcium phosphate material. Other steps may be needed in order to add other materials such as bioactive agents. In one embodiment, the support structure may include PLA/PGA polymeric material that can be made tacky by immersing it briefly in dichloromethane or another solvent. Once the polymeric material is tacky, the calcium phosphate material can be contacted with the tacky struts to lightly coat the support structure. This method of attachment preserves the surface characteristics of the particles while effectively attaching them to the polymer scaffold. In another embodiment, the support structure may be coated with an adhesive material, preferably bioremovable adhesive material, and then lightly coated with the calcium phosphate material. In another embodiment, the support structure is heated while levitated in a fluidized bed such that the calcium phosphate material adheres to the softened strut surfaces.

The particles of calcium phosphate material may be applied using any of a number of systems and techniques. For example, in one embodiment, the support structure may be placed in a fluidized bed with the calcium phosphate material. As the air flow circulates in the fluidized bed, the calcium phosphate is deposited on the exposed surfaces in the pores and on the exterior of the support structure. The amount of calcium phosphate material is selected so that a light coating is formed of separate and discrete individual particles or separate and discrete clumps of particles of calcium phosphate as described above.

The composite scaffold may have any suitable shape depending on the application. The composite scaffold may be initially molded to have the desired shape or may be cut from a larger piece of material to the desired shape. The composite scaffold may be cut before or after the coating of calcium phosphate material is applied. The composite scaffold may also be a combination of two or more pieces that are coupled together to form the final shape. FIG. 1 shows a number of examples of the shapes that the composite scaffold may have.

The composite scaffold may have a variety of clinical uses. One important example is to repair and/or regenerate articular cartilage. The scaffolds also are useful in treating cartilage defects such as those which result from rheumatoid arthritis, osteoarthritis and trauma. Cells useful for seeding in such circumstances are chondrocytes and cartilage cell precursors.

The composite scaffold can be seeded with cartilage-forming cells in order to optimize chondrogenesis. Desirably, this seeding is accomplished by placing the composite scaffold into contact with a source of the host's own cartilage-forming cells (e.g., chondrocytes) or precursors thereto. Such cells are found in cartilage-associated blood or fluids, including exogenous fluids that have been in contact with cartilage or cartilagenous materials. Thus, fluids that have been in contact with the perichondrium, cartilage, or marrow typically contain such cells.

In many cases, seeding can be accomplished by placing the composite scaffold into contact with the breached region of the perichondrium. In other cases, it will be useful to surgically prepare a seating for the composite scaffold within existing cartilagenous tissue by removing a portion of the cartilage at the implant site.

In some embodiments, additional steps may be taken to augment chondrogenesis associated with the seeded composite scaffold. For example, cartilage-forming cells harvested from the patient may be introduced into the device in addition to (or as an alternative to) cells that impregnate it after implantation in vivo. Alternatively or additionally, trophic factors or cartilage growth-inducing factors may be incorporated into or onto the device.

It should be clear that autologous cells are not required to seed the composite scaffold employed in cartilage-forming applications. Non-autologous cells may also be used so long as the cells are selected and the composite scaffold is formulated so that a desired amount of cartilage regeneration occurs prior to host rejection of the cartilage-forming cells. Thus, cells or tissues obtained from primary sources, cells lines, or cell banks are useful in the practice of this embodiment.

Other uses include repairing and/or regenerating bone defects caused by trauma, bone tumor resection, in the case of joint fusion and spinal fusion for non-healing fractures and osteoporotic lesions. As previously explained, the composite scaffold may be seeded with bone cells (osteoblasts and osteocytes) and bone cell precursors (mesenchymal stem cells from bone marrow, periosteum, endosteum, etc.) before implantation. The composite scaffold also may be used to repair defects and damage to muscle and other soft tissues such as results from trauma, burns, ulcers (diabetic ulcers, pressure sores, venus, stasis ulcers, etc.). In this case, the composite scaffold can be seeded with, for example, dermal fibroblasts, keratinocytes, and skeletal muscle cells. Likewise, damage to visceral organs including liver damage, heart attack damage, and damage resulting from intestinal cancer or intestinal ulcer may be treated with the composite scaffold. In these instances, the composite scaffold can be seeded with cells such as hepatocytes, cardiac muscle cells, intestinal cells, etc.

The composite scaffold may be used to culture cells in vitro with the purpose of creating tissue constructs for repairing tissues and organs in vivo. The composite scaffold may be used to promote tissue culture of committed cells and/or differentiation of precursor cells. Thus, the composite scaffold can be used in virtually all instances where it is desirable to provide a substrate for the growth of cells onto or into a tissue replaceable matrix.

It should be appreciated that the cell seeded composite scaffold can be usefully employed in any of a variety of in vivo and in vitro systems. For example, the material may be used to deliver biologically active agents or cells to any of a variety of sites in a patient. Alternatively or additionally, the material may be used in bone tissue or repair applications or augmentation plastic therapy in vivo. The material may also be employed as a cell encapsulation membrane or matrix, or in artificial organ construction or repair.

All patents, patent applications, or other documents that are referenced in the text of this document are hereby incorporated by reference herein in their entireties (all drawings, text, and other subject matter). In the event of a conflict, the subject matter explicitly recited or shown herein controls over any subject matter incorporated by reference. All definitions of a term (express or implied) contained in any of the subject matter incorporated by reference herein are hereby disclaimed. The paragraphs shortly before the claims dictate the meaning to be given to any term explicitly recited herein subject to the disclaimer in the preceding sentence.

EXAMPLES

The following examples are provided to further illustrate the subject matter disclosed herein. These examples should not be considered to limit the claims or scope of this disclosure in any way. The following examples describe five experiments that demonstrate the concept of creating a coating of discrete particles of calcium phosphate material on polymer support structures that are resilient and porous. The support structures in some of the examples include materials that are not bioremovable. However, the support structures demonstrate the process and the end product that can be made using the process. Also, it should be appreciated that bioremovable materials may be substituted for those materials that are not bioremovable.

The following support structures were tested as described in the following:
1. A disk of fine polyurethane foam (80 pores per inch) coated with PLA/PGA polymeric material.
2. A disk of coarse polyurethane foam (10 pores per inch) coated with PLA/PGA polymeric material.
3. One cube each of fine and coarse polyurethane foam coated with PLA/PGA polymeric material and coupled together.
4. A molded ordered porous structure (MOPS) of PLA/PGA polymeric material. The molded ordered porous structure was formed in accordance with the principles described in U.S. patent application Ser. No. 11/848,163, entitled "Methods, Tools, and Products for Molded Ordered Porous Structures,", filed on Aug. 30, 2007, and naming Majid Entezarian et al. as inventors, which is incorporated herein by reference in its entirety.

The polyurethane foam used in the first three listed support structures was coated with PLA/PGA to facilitate the attachment of amorphous calcium phosphate powder to the struts and to simulate a biocompatible material. The polymer coating was applied by dipping the polyurethane foams into a solution of 50% PLA/50% PGA polymeric material (Lakeshore Biomaterials) dissolved in dichloromethane (Aldrich). These support structures were allowed to dry to a sticky or tacky stage after being dipped in the polymer coating solution. Support structure four was soaked in acetone to make the surfaces of its struts tacky or sticky.

Each support structure was then coated with calcium phosphate particles as follows. Support structures one, two, and four were placed one at a time into the cone of a small-scale fluidized bed apparatus. The air pressure in the fluidized bed was set high enough to keep the support structures aloft. Once the support structures were in place in the fluidized bed, but before the tacky surfaces were dry, amorphous calcium phosphate powder was added and the cone was covered with a fine mesh to keep the powder from escaping while maintaining air flow. The materials were left in the fluidized bed for approximately one minute. Support structure three was coated with calcium phosphate by dipping and coating each piece of foam separately in a plate of the powder. The sides of the pieces that were to be joined with the polymer coating solution were rewetted and pressed together.

Figure 3:
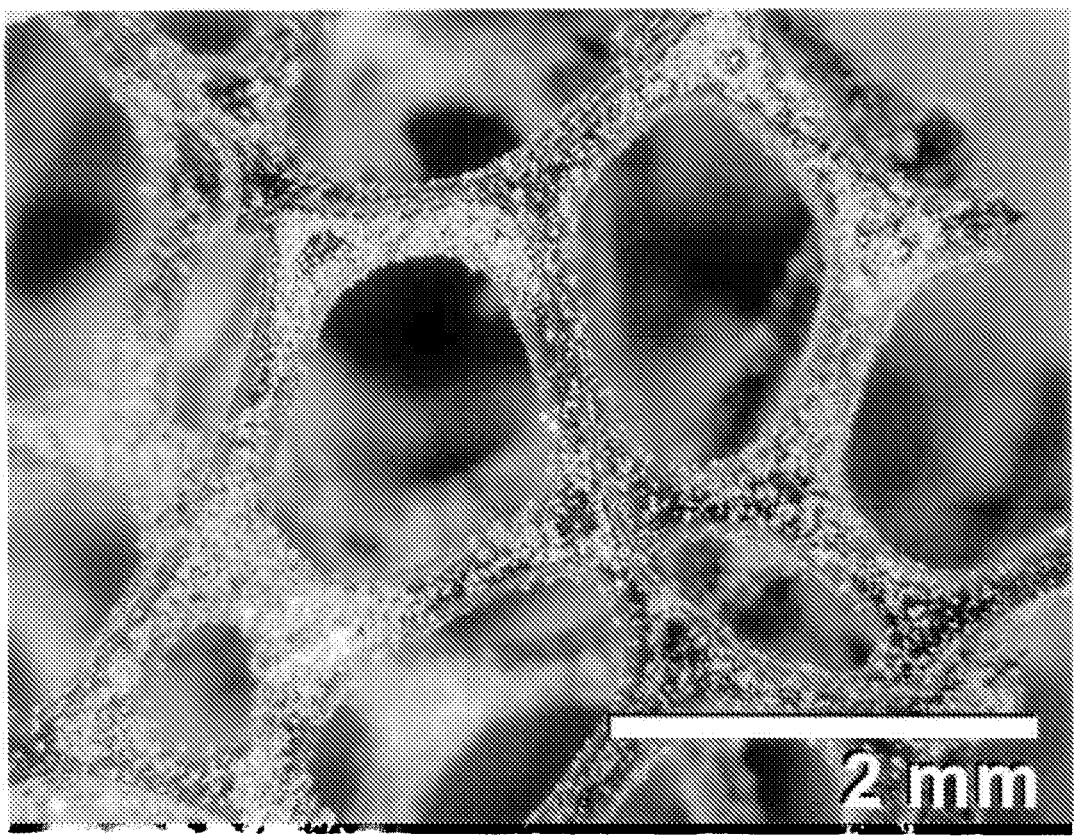
FIG. 3 is a photograph of a coarse pore polyurethane foam that is coated with a light coating of amorphous calcium phosphate.
Figure 4:
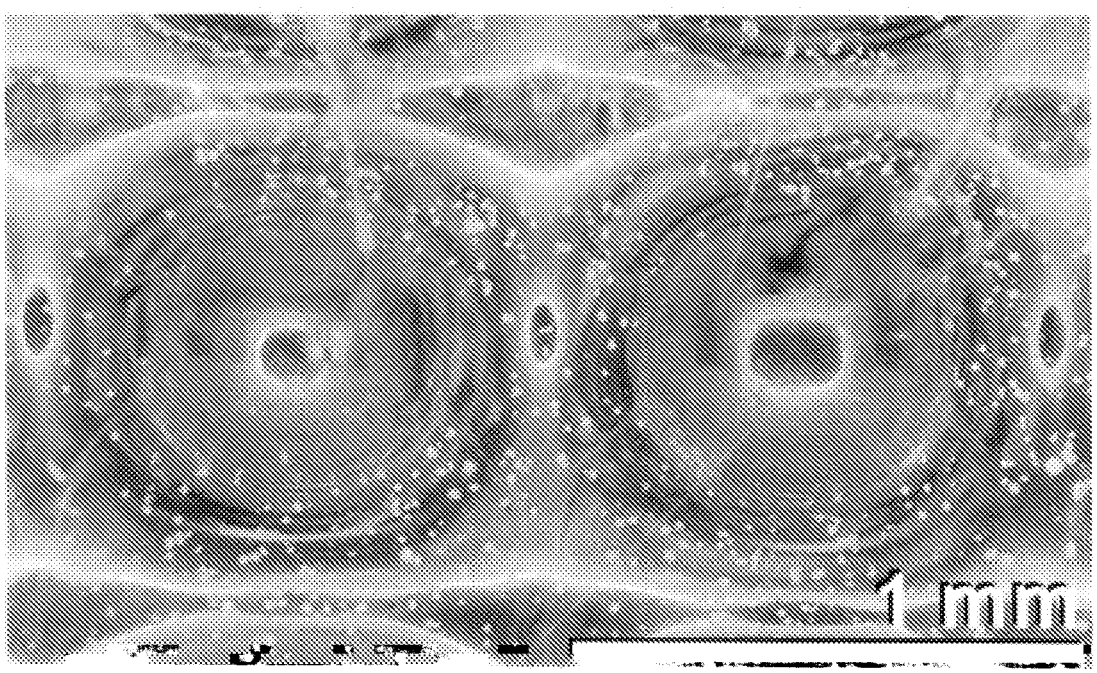
FIG. 4 is a photograph of an injection molded bioremovable polymer that is coated with a light coating of amorphous calcium phosphate.

This procedure produced support structures where the surface of the struts in the support structure were lightly coated with the amorphous calcium phosphate powder (i.e., light distribution of calcium phosphate powder). The light coating left a substantial amount of the strut surfaces exposed, which allows cells to easily cling to the exposed surfaces and to grow along and around them. FIG. 3 is a photograph of the coarse foam support structure lightly coated with amorphous calcium phosphate particles, and FIG. 4 is a photograph of the MOPS support structure lightly coated with amorphous calcium phosphate particles. Support structures one, two, and three retained their original spongy resilience even after being coating with the amorphous calcium phosphate material.

It should be noted that for purposes of this disclosure, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. The subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

As used herein, spatial or directional terms, such as "left," "right," "front," "back," and the like, relate to the subject matter as it is shown in the drawing FIGS. However, it is to be understood that the subject matter described herein may assume various alternative orientations and, accordingly, such terms are not to be considered as limiting. Furthermore, as used herein (i.e., in the claims and the specification), articles such as "the," "a," and "an" can connote the singular or plural. Also, as used herein, the word "or" when used without a preceding "either" (or other similar language indicating that "or" is unequivocally meant to be exclusive—e.g., only one of x or y, etc.) shall be interpreted to be inclusive (e.g., "x or y" means one or both x or y). Likewise, as used herein, the term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

What is claimed is:

1. A composite scaffold comprising:
    a resilient support structure that is porous and bioremovable, the resilient support structure including a bioremovable polymeric material;
    a plurality of particles of calcium phosphate material that form a discontinuous coating of discrete particles on the resilient support structure such that the calcium phosphate material resists breaking when the resilient support structure flexes.

2. The composite scaffold of claim 1 wherein the particles from the plurality of particles are porous.

3. The composite scaffold of claim 2 wherein each of the particles have a pore size of approximately 0.01 micron to 1 micron.

4. The composite scaffold of claim 2 wherein a bioactive agent is positioned in the pores of the particles.

5. The composite scaffold of claim 1 wherein the composite scaffold includes a bioactive agent that promotes cartilage growth.

6. The composite scaffold of claim 5 wherein the bioactive agent includes collagen.

7. The composite scaffold of claim 1 wherein the plurality of particles include tricalcium phosphate material.

8. The composite scaffold of claim 1 wherein the calcium phosphate material is amorphous calcium phosphate material.

9. The composite scaffold of claim 1 wherein the resilient support structure has a reticulated porous structure and/or is assembled by coupling a plurality of rods together.

10. The composite scaffold of claim 1 wherein the resilient support structure is injection molded.

11. The composite scaffold of claim 1 wherein the composite scaffold includes a plurality of cells that promote repair and/or regeneration of articular cartilage.

12. A composite scaffold comprising:
    a resilient support structure including a bioremovable polymeric material, the resilient support structure being coated with calcium phosphate material;
    wherein the composite scaffold is configured so that the calcium phosphate material resists breaking when the resilient support structure flexes.

13. The composite scaffold of claim 12 wherein the calcium phosphate material forms a coating of separate and discrete particles of calcium phosphate material and/or separate and discrete clumps of particles of calcium phosphate.

14. The composite scaffold of claim 12 wherein the resilient support structure is coated with a plurality of porous particles of calcium phosphate material.

15. The composite scaffold of claim 14 comprising a bioactive agent positioned in the pores of the porous particles of calcium phosphate material.

16. The composite scaffold of claim 12 wherein the calcium phosphate material is amorphous calcium phosphate material.

17. The composite scaffold of claim 12 wherein the resilient support structure has a reticulated porous structure and/or is assembled by coupling a plurality of rods together.

18. The composite scaffold of claim 12 wherein the composite scaffold includes a plurality of cells that promote repair and/or regeneration of articular cartilage.

19. A composite scaffold comprising:

a bioremovable polymeric material that forms a support structure;

a plurality of particles of calcium phosphate material that form a discontinuous coating of discrete particles over the support structure.

20. The composite scaffold of claim 19 wherein the particles from the plurality of particles are porous.

21. The composite scaffold of claim 20 comprising a bioactive agent positioned in the pores of the particles.

22. The composite scaffold of claim 19 wherein the calcium phosphate material is amorphous calcium phosphate material.

23. The composite scaffold of claim 19 wherein the support structure has a reticulated porous structure and/or is assembled by coupling a plurality of rods together.

24. The composite scaffold of claim 19 wherein the support structure is injection molded.

25. The composite scaffold of claim 19 wherein the composite scaffold includes chondrocytes.

* * * * *